United States Patent
Bertocci (10) Patent No.: US 9,067,023 B2
(45) Date of Patent: Jun. 30, 2015

(54) ERGONOMIC SYRINGE AND ADAPTOR

(71) Applicant: University of Lousiville Research Foundation, Inc., Nashville, TN (US)

(72) Inventor: Gina E. Bertocci, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 387 days.

(21) Appl. No.: 13/676,810

(22) Filed: Nov. 14, 2012

(65) Prior Publication Data

US 2013/0131606 A1 May 23, 2013

Related U.S. Application Data (60) Provisional application No. 61/562,167, filed on Nov. 21, 2011.

(51) Int. Cl.
*A61M 5/315* (2006.01)

(52) U.S. Cl.
CPC ........... *A61M 5/31515* (2013.01); *A61M 5/315* (2013.01); *A61M 5/31513* (2013.01)

(58) Field of Classification Search
CPC ............ A61M 5/315; A61M 5/31513; A61M 5/31515
USPC ......... 604/181, 187, 207, 212, 214, 218, 222, 604/227, 228
See application file for complete search history.

(56) References Cited

U.S. PATENT DOCUMENTS

| | | |
|---|---|---|
| 3,325,061 A | 6/1967 | Ellsworth |
| 3,583,399 A | 6/1971 | Ritsky |
| 3,618,603 A | 11/1971 | Levenson |
| 3,758,006 A | 9/1973 | Gravlee |
| 3,797,487 A | 3/1974 | Schmidt |
| 3,819,091 A | 6/1974 | Hollender |
| 3,835,835 A | 9/1974 | Thompson et al. |
| 3,848,579 A | 11/1974 | Villa-Real |
| 3,910,273 A | 10/1975 | Arlers |
| 3,949,748 A | 4/1976 | Malmin |
| 3,990,446 A | 11/1976 | Taylor |
| 4,216,771 A | 8/1980 | Arlers et al. |
| 4,263,911 A | 4/1981 | McCormack et al. |
| 4,333,456 A | 6/1982 | Webb |
| 4,448,206 A | 5/1984 | Martell |
| 4,484,915 A * | 11/1984 | Tartaglia ..................... 604/227 |
| 4,563,178 A | 1/1986 | Santeramo |
| 4,594,073 A | 6/1986 | Stine |
| 4,639,248 A | 1/1987 | Schweblin |
| 4,664,128 A | 5/1987 | Lee |
| 4,766,908 A | 8/1988 | Clement |

(Continued)

FOREIGN PATENT DOCUMENTS

| | | |
|---|---|---|
| WO | WO2004060450 A1 | 7/2004 |
| WO | WO2012159211 A1 | 11/2012 |

*Primary Examiner* — Theodore Stigell
*Assistant Examiner* — Amber Stiles
(74) *Attorney, Agent, or Firm* — Wyatt, Tarrant & Combs, LLP; Stephen C. Hall (57) ABSTRACT

An ergonomic syringe includes a slide member, wherein force exerted on the slide member causes movement of a syringe plunger within a hollow or partially hollow syringe barrel, for withdrawing fluid from a source into the syringe, and also includes a reusable adaptor for use with existing conventional syringes, which has a ring that wholly or partially encircles the barrel and indirectly attaches to a plunger flange.

8 Claims, 10 Drawing Sheets

(56) References Cited

U.S. PATENT DOCUMENTS

| | | | |
|---|---|---|---|
| 5,115,816 A | 5/1992 | Lee | |
| 5,135,511 A * | 8/1992 | Houghton et al. | 604/220 |
| 5,246,011 A | 9/1993 | Caillouette | |
| 5,395,345 A | 3/1995 | Gross | |
| 5,469,860 A | 11/1995 | De Santis | |
| 5,582,595 A | 12/1996 | Haber et al. | |
| 5,651,372 A | 7/1997 | Caillouette | |
| 5,814,023 A | 9/1998 | Fulk et al. | |
| 5,830,152 A | 11/1998 | Tao | |
| 5,833,668 A | 11/1998 | Aguilar | |
| 5,902,278 A | 5/1999 | Aguilar | |
| 6,231,550 B1 | 5/2001 | Laughlin | |
| 6,245,046 B1 | 6/2001 | Sibbitt | |
| 6,283,941 B1 | 9/2001 | Schoenfeld et al. | |
| 6,368,308 B1 | 4/2002 | Nerney | |
| 6,616,634 B2 | 9/2003 | Benz et al. | |
| 6,669,672 B2 | 12/2003 | Wu | |
| 6,719,735 B1 | 4/2004 | Gammon | |
| 7,118,556 B2 | 10/2006 | Nerney | |
| 7,534,234 B2 | 5/2009 | Fojtik | |
| 7,967,793 B2 | 6/2011 | Sibbitt, Jr. et al. | |
| 2004/0039345 A1 | 2/2004 | Benz et al. | |
| 2004/0073172 A1 | 4/2004 | Acha Gandarias | |
| 2004/0116875 A1 | 6/2004 | Fischer et al. | |
| 2009/0093787 A1 | 4/2009 | Barbour | |
| 2011/0160674 A1 | 6/2011 | Holmes et al. | |

\* cited by examiner

ERGONOMIC SYRINGE AND ADAPTOR

CROSS REFERENCE TO RELATED APPLICATIONS

This application claims priority to U.S. Provisional Application No. 61/562,167, filed Nov. 21, 2011.

FIELD OF INVENTION

The presently disclosed technology relates, generally, to syringe products. More particularly, it relates to syringe products that facilitate ergonomic operation, e.g., single-handed operation of a syringe, and other advantages such as enhanced control and stability.

BACKGROUND

Throughout the descriptions herein, reference is made both to a proximal end and a distal end of various parts of a syringe. Proximal is the end closer to a user's (i.e., an operator's) body when operating a syringe. Distal is closer to the end from which fluid either exits the syringe during injection or enters the syringe during withdrawal.

A syringe typically contains several parts. One is a cylindrical barrel that is substantially hollow. Another is a plunger that partially fits within the hollow space of the barrel. Syringes are used to inject and/or withdraw fluids in various sectors such as, for example, laboratory, human medicine and veterinary medicine fields. The injection and/or withdrawal of fluids can be into/from a blood vessel, tissue, or other body region of a patient.

The plunger either pushes fluid out of the barrel during injection, or pulls fluid into the barrel during withdrawal. Many syringes have a hollow needle or cannula permanently or detachably connected at the distal end of the barrel. Injecting fluid from a syringe is accomplished by pushing the plunger further into the barrel, where the fluid is located. This action reduces the volume and forces fluid to be expelled through an opening of the barrel. Withdrawing fluid from an external source into a syringe is accomplished by partially drawing the plunger from the barrel to create a vacuum, which causes fluid to flow from the external source into the barrel. Typically, syringes have markings on the barrel that signify a quantity of fluid contained therein.

Some syringe plungers have a flange at the proximal end, herein referred to as a plunger flange. In conventional use, one holds or otherwise contacts a surface of the plunger flange to exert a proximal force and withdraw the plunger from the barrel during fluid withdrawal, or to exert a distal force and push the plunger further into the barrel during fluid injection. Some syringes have a flexible, elastomeric member, referred to herein as a sealing member, which fits over the distal-most end of the plunger and facilitates the creation of the vacuum as a user withdraws the plunger. For example, phlebotomy is the withdrawal of blood from a blood vessel, typically a vein. Fine needle aspiration (FNA) means the withdrawal of material from body tissue so that cells can be studied under a microscope. Arthrocentesis involves aspirating a joint to either collect a fluid sample for diagnostic purposes, or to drain effusions from the joint space. Phlebotomy, FNA, and arthrocentesis are situations in which an ergonomic syringe and adaptor would facilitate the withdrawal of fluids from a patient.

Various techniques and finger/hand positions are commonly used for moving the plunger in the proximal direction in order to create the vacuum that withdraws fluid from an external source into the barrel. In conventional operation, a user often must employ a two-handed technique, particularly for withdrawing fluid, in which the user grasps the outer surface of the barrel with fingers of a first hand, while grasping the plunger flange at the proximal end with fingers of a second hand. The user then holds the barrel in a relatively stationary position with the first hand while pulling or otherwise exerting force on the plunger flange in a proximal direction with the second hand to further withdraw the plunger from the barrel. However, a two-handed technique has several disadvantages. One is that, by grasping the plunger flange with one hand and the barrel with the other, the user does not have a free hand available to stabilize the patient's body region or part from which fluid is being withdrawn, which is important in many respects, including in veterinary medicine.

Therefore, instead of using both hands to operate the syringe, in some respects it is more desirable to use only one hand. A one-handed technique provides the user a free hand for performing additional tasks, such as holding onto and thereby stabilizing the patient's limb, tissue mass, or other body region. It is also desirable in some situations to have one hand free to handle other equipment that is used when fluid is withdrawn from a patient.

Notwithstanding, a conventional syringe, such as is generally commercially available and used by medical providers and laboratory personnel, does not facilitate a one-handed technique, especially for withdrawing of fluids. This is because, as a user withdraws the plunger flange proximally along the longitudinal axis of the barrel, the distance necessarily increases between the barrel and the plunger flange. In other words, since the plunger flange is located proximal to the barrel, in the direction that the plunger must travel, it requires the user to move his or her fingers through an over-extended range of motion in order to maintain a vacuum and withdraw the plunger thereby pulling fluid or cells into the barrel.

This maneuver can be difficult to accomplish for those with normal hand/finger dexterity, and may be impossible for those with limited hand/finger dexterity and/or strength such as one with arthritis, or whose fingers are relatively short in length. An ergonomic syringe and adaptor, as described herein, helps solve this difficulty. Also, because it is more effective to use the syringe in a one-handed technique, for example to withdraw fluids, the maneuver can be accomplished more ergonomically and rapidly. This reduces the amount of time that a patient must be restrained or encouraged to remain still. In an emergency, the time savings has the potential to improve outcomes. Likewise, an ergonomic syringe, and an adaptor for use with existing conventional syringes, reduce potential trauma to a patient's blood vessel, tissue, or other body region during withdrawal of fluids, given that there is greater efficiency in stabilizing the barrel and associated needle placement in a one-handed technique. Moreover, those with limited hand/finger dexterity, strength, or digit length may be able to accomplish the task of one-handed fluid withdrawal, whereas otherwise they may not be capable of doing so with a conventional syringe. Also, it is expected that repetitive use injuries to users may be reduced due to ergonomic improvements over conventional syringes.

It will be understood by those having ordinary skill in the art, that conventional syringes are designed primarily for injecting fluids, for example vaccines or medications. Such designs, however, are not as suitable for withdrawing fluids because of the direction of movement of the plunger. With a one-handed syringe technique, because the fingers must spread and become over-extended, it becomes more likely that a user's hand or fingers will slip from contact with the barrel and/or plunger flange during withdrawal. Additionally, as the distance increases, it becomes more difficult to apply sufficient force to the plunger flange, a task that some users (e.g., those having shorter fingers or limited dexterity and/or strength) may not be able to accomplish.

SUMMARY OF INVENTION

Based upon the foregoing, there are significant needs for ergonomic syringes, as well as adaptors that will interface with conventional syringes, to provide increased user control and stability when exerting mechanical force needed to move the plunger while withdrawing fluids, that reduce the overall range of motion that the finger must travel in order to exert such force, to reduce repetitive strain on the user during these maneuvers, to make the use of syringes more efficient and less difficult, to promote one-handed use, and to otherwise provide advantages for users having limited hand/finger strength. Further, there is a need to practically convert conventional syringes, which are designed to inject fluids, into syringes that are ergonomically designed to withdraw fluids and other matter using a one-handed syringe technique. The present embodiments, as described and claimed herein, meet these needs.

Accordingly, various embodiments and alternatives of an ergonomic syringe and adaptor, as described herein, improve and facilitate the withdrawal of fluids. By way of illustration only, the disclosed embodiments allow for one-handed operational functionality; incorporate features that promote ergonomically desirable and consistent finger placement on the syringe barrel; facilitate a user's ability to stabilize the syringe when in use for example, when introducing a hypodermic needle into the body of the patient; provide a contoured surface tailored to the functional position of the fingers and hand on the outer surface of the barrel; and/or reduce the range of motion that a finger in contact with the plunger flange must undergo in order to apply sufficient force to move the plunger within the barrel, thus creating a vacuum for withdrawing fluid from an external source. As used herein, the word "finger" includes all fingers or phalanges including the thumb, index, middle, ring, and pinky fingers (i.e., $1^{st}$ through $5^{th}$ digits of the hand). It is expected that such embodiments, as described herein, will tend to reduce repetitive use injuries that are sometimes experienced by phlebotomists and other users of syringes. It is also expected that such embodiments will enable those with limited dexterity and/or reduced hand/finger strength to accomplish the maneuvers associated with fluid withdrawal.

BRIEF DESCRIPTION OF THE DRAWINGS

The written description of multiple embodiments and alternatives, as set forth herein, will be better understood when read in connection with the appended drawings. It will be understood that the application is not limited to precise arrangements shown, nor are the illustrations intended as being drawn to scale.

MULTIPLE EMBODIMENTS AND ALTERNATIVES

The descriptions and teachings herein are suitable for the manufacture of new syringe products, yet also suitable for an adaptor that can be retrofitted or detachably secured to existing syringes, and then reused. The teachings and descriptions are particularly applicable to withdrawal of fluid from a patient's blood vessel, tissue, or other body region, as well as withdrawal of fluid from a vessel, e.g., a vial or a test tube.

Figure 1:
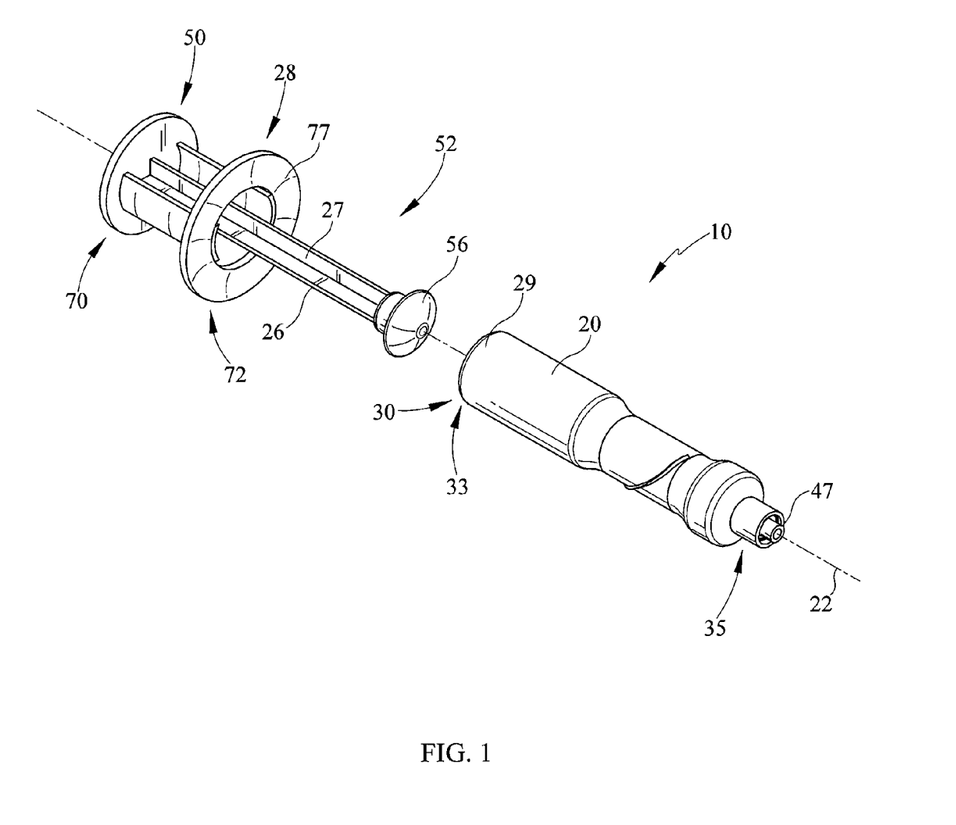
FIG. 1 is an exploded view of an ergonomic syringe with a contoured barrel, according to multiple embodiments and alternatives.

FIG. 1 is an exploded view of an ergonomic syringe 10, as described herein, according to multiple embodiments and alternatives. Syringe 10 comprises a barrel 20, having a proximal end 33 and a distal end 35. Generally, an aperture 29 is positioned at proximal end 33 of barrel 20. Syringe 10 also comprises a plunger 26, having a proximal end 50 and a distal end 52. Axis 22 extends centrally through the length of barrel 20 and plunger 26.

In some embodiments, syringe 10 also comprises slide member 28 as shown in FIG. 1. Slide member 28 comprises a proximal end 70 and a distal end 72, along with a ring 77 positioned between the two ends, at or substantially near distal end 72. Ring 77, including a distal facing surface 79 (which is labeled in FIG. 2), is adapted for engagement by one or more fingers of a user during fluid withdraw. In some embodiments, ring 77 includes a flange extending radially outward that encircles the outer cylindrical circumference of barrel 20 when plunger 26 is positioned within barrel 20. Optionally, ring 77 may have a concave surface to accommodate finger placement. In the embodiment depicted in FIG. 1, ring 77 is a unitary piece that encircles the entire 360° outer circumference of barrel 20. However, in some embodiments (not shown), ring 77 may be segmented and/or only partially encircles barrel 20.

In some embodiments, barrel 20 is generally cylindrical, having a rim 30 at its proximal end 33 which forms the periphery of aperture 29. In some embodiments, plunger 26 further comprises a sealing member 56 positioned at or near at distal end 52. Sealing member 56 is formed from materials suitable for creating and maintaining a fluid-tight seal between the distal portion of plunger 26 and the inner walls of barrel 20, e.g., rubber, polymeric, elastomeric, or other suitable materials. In some embodiments, the inner diameter of the barrel formed by rim 30 is larger than the diameter of distal end 52 of plunger 26. In this way, aperture 29 accommodates plunger 26 such that, in use, plunger 26 is at least partially inserted into the hollow space of barrel 20 for operational engagement and axial movement within the barrel. In some embodiments, plunger 26 comprises a unitary member in which a plurality of webs 27 are attached along a common edge, wherein the webs 27 extend perpendicular to axis 22, while running parallel to axis 22, to provide a sliding fit for plunger 26 within barrel 20.

As shown in FIG. 1, slide member 28 is attached to plunger at their respective proximal ends, 50 and 70. Accordingly, a force exerted upon ring 77 produces movement of slide member 28 along axis 22, thereby causing slide member 28, plunger 26, and sealing member 56, respectively, to move a substantially equal distance along the same axis. In this way, force exerted upon ring 77 determines and influences the instantaneous positions of plunger 26 and sealing member 56, respectively.

Figures 2, 2A:
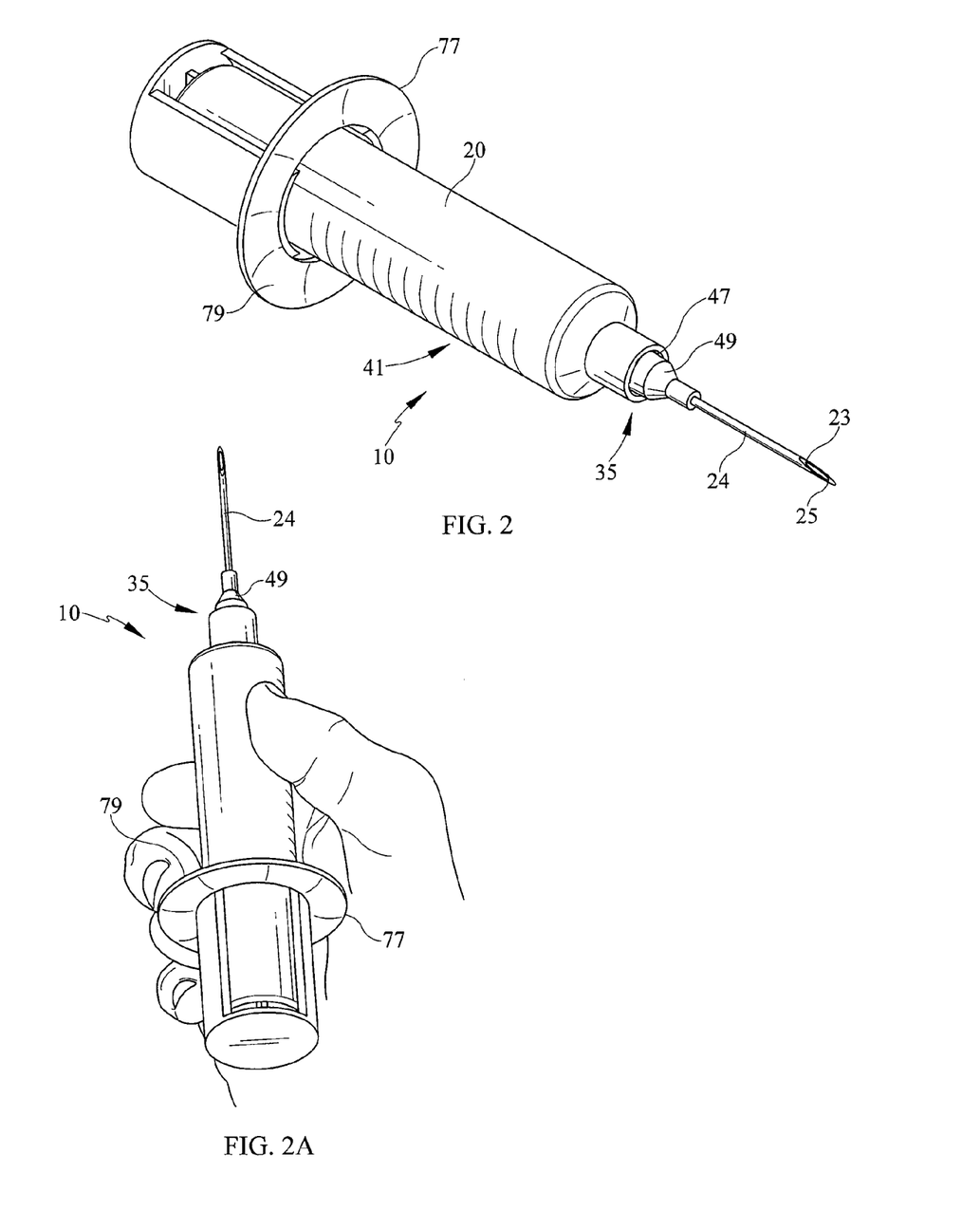
FIG. 2 is a perspective view of an ergonomic syringe, according to multiple embodiments and alternatives.
FIG. 2A is a perspective view of an ergonomic syringe that illustrates one way it can be operated by a user, according to multiple embodiments and alternatives.

As shown in FIG. 2, in most embodiments barrel 20 contains markings 41 indicating an amount of fluid contained within barrel 20. Needle attachment 49 fits into opening 47 (as also shown in FIG. 1) at the distal end 35 of barrel 20 through means that are known to those of ordinary skill in the art, e.g., a snap-fit engagement or threaded screw arrangement between needle attachment 49 and opening 47. In many embodiments, opening 47 detachably receives needle 24 using components that are known in the art, e.g., a slip tip, catheter tip, Luer-Lok® and Luer-Slip®, and needle 24 further includes a needle opening 23 comprising a beveled edge 25. FIG. 2 also illustrates ring 77 encircling the entire outer circumference of barrel 20 and the distal facing surface 79 of the ring.

Figure 3:
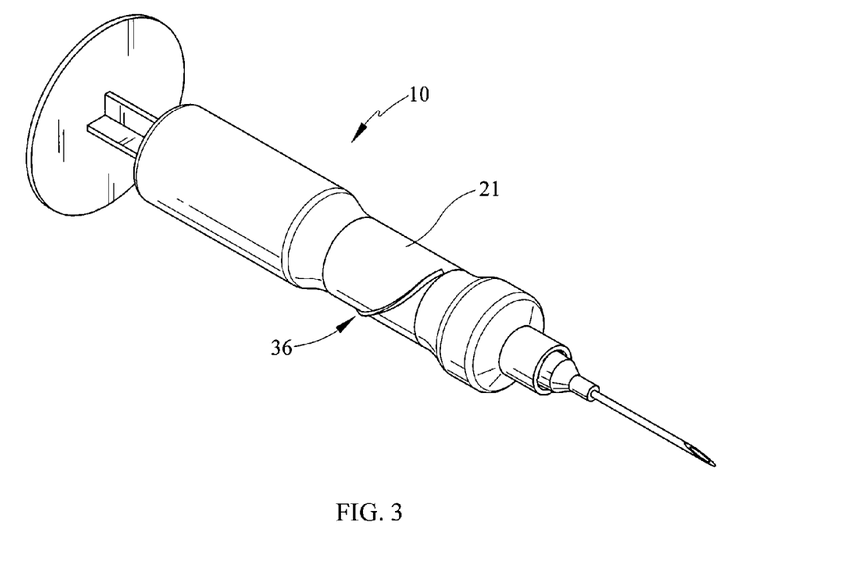
FIG. 3 is a perspective view of a contoured barrel of an ergonomic syringe, according to multiple embodiments and alternatives.
Figure 3A:
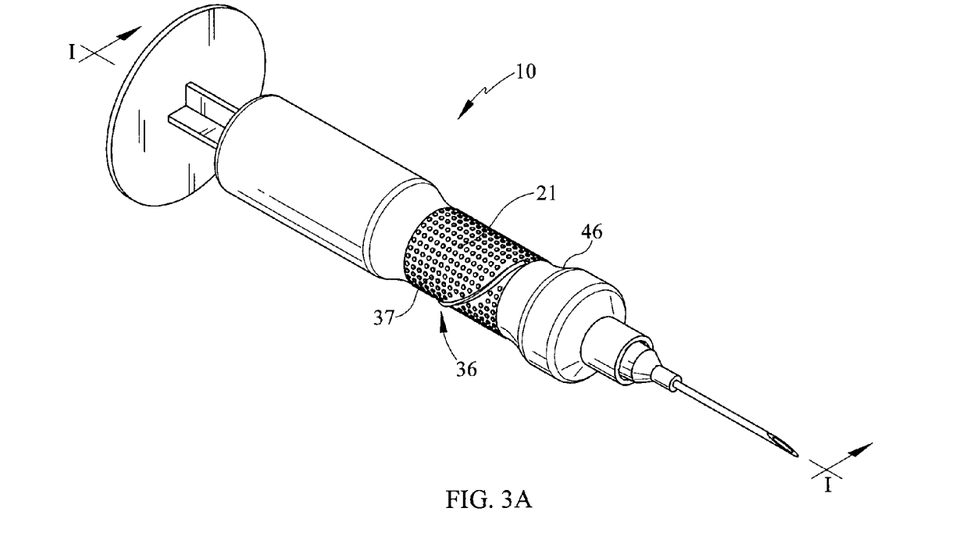
FIG. 3A is a perspective view of a contoured barrel of an ergonomic syringe, according to multiple embodiments and alternatives.

FIG. 3 and FIG. 3A, respectively, provide views of an ergonomic syringe 10, according to multiple embodiments and alternatives, wherein the barrel 20 includes at least one finger placement aid. For example, the syringe shown in both figures has a contoured barrel 21 and a finger placement guide 36 for stable and consistent contact by a user with barrel 20. In some embodiments, finger placement guide 36 is formed as a ridge to promote ergonomic engagement with a user's finger along contoured barrel 21 of syringe 10. In some embodiments, a ridge that forms finger placement guide 36 is fabricated integral to contoured barrel 21 during manufacture. Optionally, as illustrated in FIG. 3A, contoured barrel 21 includes a grip-enhancing material 37 substantially encircling at least a portion of an exterior surface of contoured barrel 21. In some embodiments, grip-enhancing material 37 is formed separately from contoured barrel 21 and fitted over the exterior surface of the barrel. Alternatively, grip-enhancing material 37 is bonded to the surface of, or otherwise applied to, contoured barrel 21. In some embodiments, the grip-enhancing material 37 comprises added material in the form of raised dots on the exterior surface of contoured barrel 21, and is accompanied by a finger placement guide 36.

Figure 4:
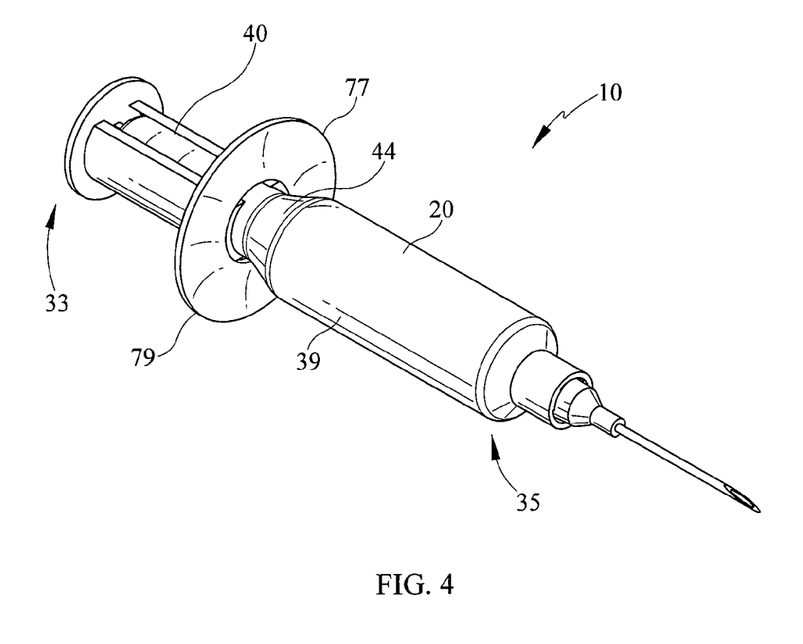
FIG. 4 is a perspective view of an ergonomic syringe, according to multiple embodiments and alternatives.
Figure 4A:
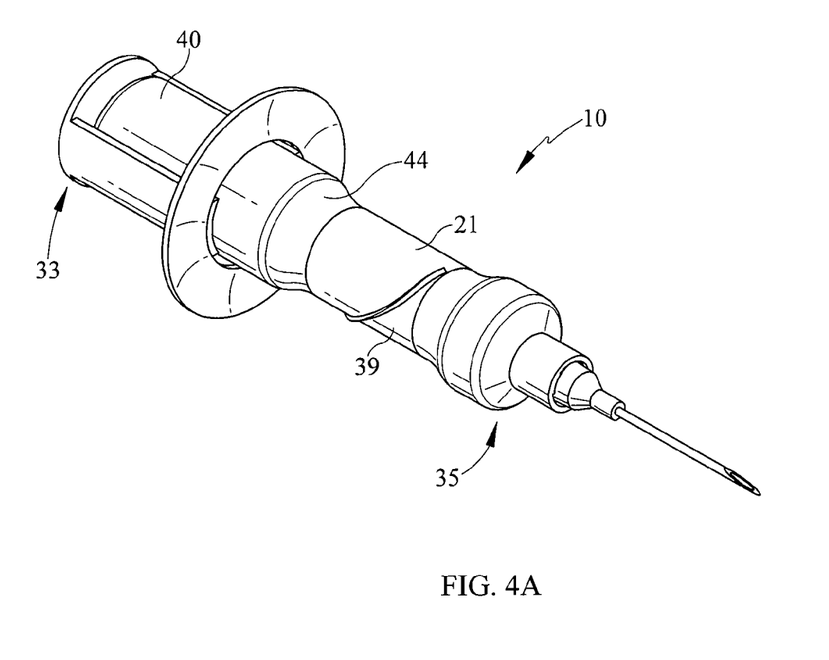
FIG. 4A is a perspective view of an ergonomic syringe, according to multiple embodiments and alternatives.

FIG. 4 and FIG. 4A, respectively, provide views of an ergonomic syringe 10, according to multiple embodiments and alternatives. FIG. 4 illustrates syringe 10 having a barrel 20, which includes a distally located first portion 39 of uniform outer circumference along its cylindrical length, and a second portion 40 of a smaller diameter along its cylindrical length, located proximally to the first portion 39. As FIG. 4 illustrates, in some embodiments, a first tapered surface 44 of barrel 20 tapers inward, from a larger diameter at a distal end 35 of barrel 20 to a lesser diameter as it extends toward a proximal end 33 of the barrel. Alternatively, surface 44 of barrel 20 tapers outward, as shown in FIG. 4A. In this way, surface 44 connects the first portion 39 with second portion 40. Optionally, the diameter of second portion 40 is greater than the diameter of first portion 39, as shown in FIG. 4A. Also as shown in FIG. 4A, in some embodiments, a second tapered surface 46 located at the distal-most end of first portion 39 gradually transitions to a diameter exceeding that of the rest of first portion. Accordingly, the difference in diameters within the first portion 39 itself also promotes ergonomic finger positioning and placement on contoured barrel 21.

It will be appreciated that ring 77 has both a distal facing surface 79 and a proximal facing surface 78, as identified by reference numerals used in FIGS. 2, 4, 5, 6, and 6A. Both surfaces can be either flat, convex, or concave, as desired.

Now referring back to FIG. 4A, during operation the combination of first portion 39 with tapered surface 44 allows for more natural placement and ergonomic positioning of fingers as selectably desired by a user. It also provides flexibility with regard to the location of fingers on barrel 20, in order to position a different finger in contact with ring 77 in a more comfortable and functional way for a particular user. This improved functional hand and finger position allows a user to exercise greater stability and improved control of the syringe during use.

Figure 5:
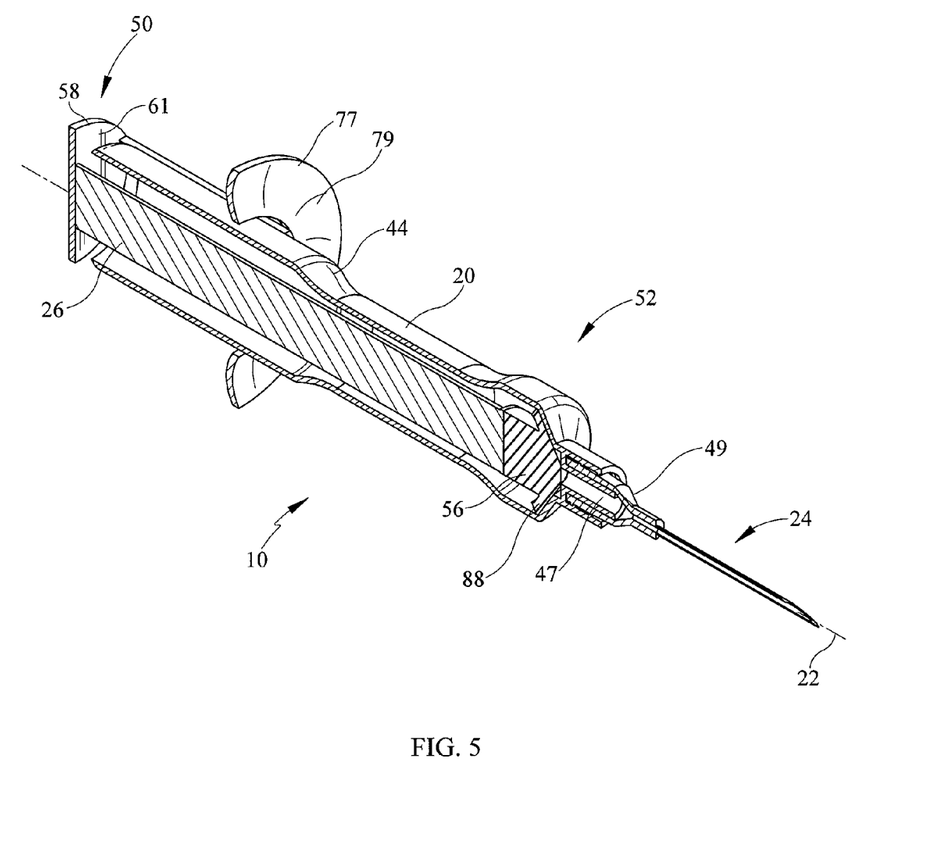
FIG. 5 is a cross-sectional perspective view of an ergonomic syringe, taken along line I-I of FIG. 4A, according to multiple embodiments and alternatives.

FIG. 5 is a cross-sectional view of an ergonomic syringe 10 taken longitudinally along line I-I of FIG. 4A, with certain elements that were also depicted in FIG. 1. In this view, needle attachment 49 is shown engaged with opening 47 at distal end of barrel 20. Plunger 26 is substantially contained within the hollow space of barrel 20. Distal facing surface 79 of ring 77 is positioned proximally of sealing member 56 with respect to axis 22. In some embodiments, ring 77 is positioned substantially at the distal end of slide member 28, and encircles the outer cylindrical circumference of barrel 20. Plunger 26 comprises a substantially elongate body capable of movement within the hollow space of barrel 20, along axis 22, and also includes sealing member 56 at its distal end 52. As plunger 26 is withdrawn axially, sealing member 56 remains in contact with the inner wall of barrel 20.

As shown in FIG. 5, in some embodiments, plunger 26 has a plunger flange 58 at its proximal end 50. Plunger flange 58 has a distal facing surface 61 that faces distally, and a proximal facing surface 63 (as seen in FIG. 6A) facing proximally. In some techniques, a user places two fingers in contact with barrel 20, and places a third finger in contact with distal facing surface 79 of ring 77 in order to exert force to plunger flange 58, thus moving it proximally along axis 22 in order to withdraw plunger 26 from barrel 20. In this regard, it will be appreciated that a degree of variability exists in user technique. For example, third finger does not necessarily mean the middle finger, but rather a different finger than the two placed in contact with barrel 20. If fluid is injected into a patient, a user places two fingers in contact with barrel 20, and places a third finger in contact with proximal facing surface 78 of ring 77. Exerting force upon proximal facing surface 78 in a distal direction causes plunger 26 to move into, or further into, barrel 20. This reduces the volume inside barrel 20 and causes fluid to be dispensed from the barrel through opening 47. Optionally, when needle 24 is connected to barrel 20 via needle attachment 49, it allows fluid that is being injected to exit the needle through opening 23.

In embodiments having a contoured barrel 21 or a variable diameter barrel 20 (such as those shown in FIGS. 3, 3A, 4, 4A, 5, and 6), the sealing member 56 may include a resilient and flexible flange 88 (shown in FIG. 5) extending about its periphery. Flange 88 maintains a fluid-tight seal between sealing member 56 and the inner walls of barrel 20 as the distal portion of plunger 26 moves along axis 22 from a portion of the barrel having a larger diameter into a portion of the barrel having a lesser diameter, and vice versa. Suitable materials for forming flange 88 include rubber, polymeric, elastomeric, and other materials having sufficient elastic recovery after deformation to maintain a fluid-tight seal under pressure and vacuum.

Figure 10:
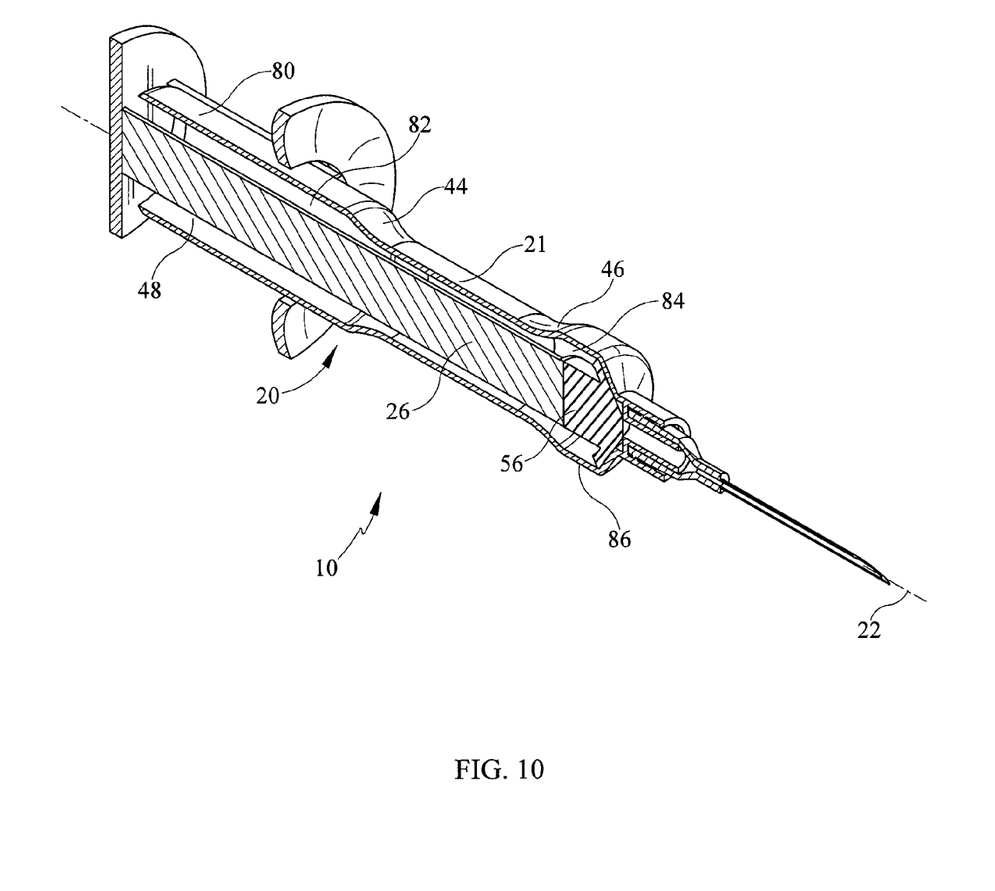
FIG. 10 is a cross-sectional perspective view of an ergonomic syringe of the kind shown in FIG. 4A, taken along line I-I, according to multiple embodiments and alternatives.

Alternatively, for embodiments in which syringe 10 has a contoured barrel 21, or a barrel of varying diameter, a separate outer diameter barrel wall is provided where surface 44 of barrel 20 begins to taper from one barrel diameter to another barrel diameter, as shown in various figures, including FIG. 4A and FIG. 10. Referring to FIG. 10, a constant diameter inner barrel wall 48 defines the internal space within barrel 20 through which plunger 26 and sealing member 56 travel axially. Outer barrel walls 80, 86 are formed where surfaces 44, 46 taper from contoured barrel 21. Cavities 82, 84 are formed between constant diameter barrel wall 48 and outer barrel walls 80, 86. Cavities 82, 84 may be void, air-filled spaces or, alternatively, contain solid material such as, for example, the same material used to form barrel 20.

Figure 6:
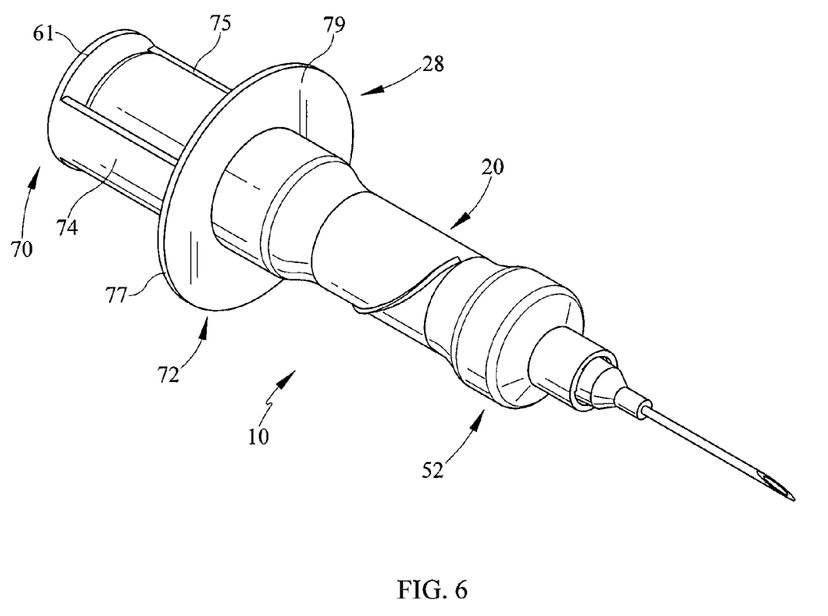
FIG. 6 is a perspective view of an ergonomic syringe, according to multiple embodiments and alternatives.
Figure 6A:
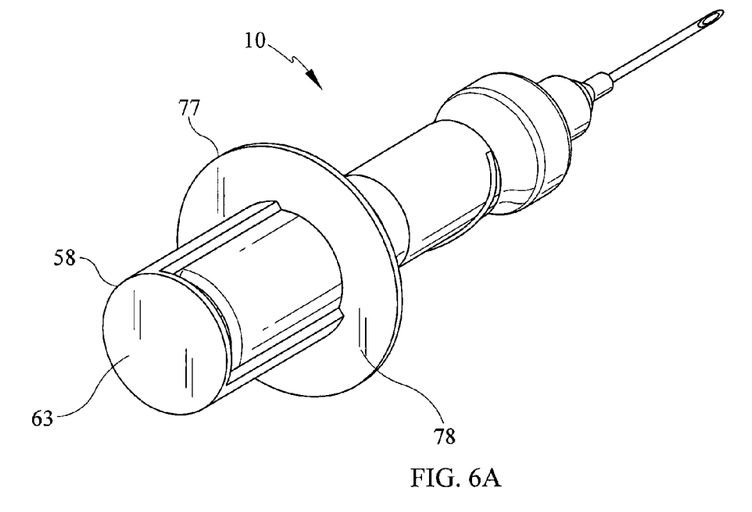
FIG. 6A is a rear-facing perspective view of an ergonomic syringe, according to multiple embodiments and alternatives.

Turning now to FIG. 6, in some embodiments slide member 28 is formed integrally with the fabrication of plunger 26. Alternatively, slide member 28 is fabricated separately from plunger 26. Generally, slide member 28 has a proximal end 70 and a distal end 72, with ring 77 being positioned at or near distal end 72. In some embodiments, the ring 77 encircles the entire 360° outer cylindrical circumference of barrel 20. Ring 77 further comprises a proximal facing surface 78 (as seen in FIG. 6A) and a distal facing surface 79. FIG. 6A also provides a view of proximal facing surface 63 of plunger flange 58.

It is often desirable to withdraw or partially withdraw plunger 26 from barrel 20 employing a one-handed technique. In order to do so, as shown in FIG. 2A, a user may place two fingers (one being the thumb, in this figure) in contact with barrel 20, at a position distal to ring 77, and place a third finger or fingers in contact with distal facing surface 79 and exert force there, in order to move the plunger in the proximal direction. Compared to a conventional syringe, as further shown in FIG. 2A, the third finger contacts the distal facing surface 79 of slide member 28 instead of having to extend to the plunger flange 58 (shown in FIG. 5) of plunger 26. The distance between the fingers in contact with barrel 20 and the distal facing surface 79 of slide member 28 is less, so a user does not have to reach as far with the third finger in order to contact the distal facing surface. This is illustrated by the fact that, with a conventional syringe, the plunger flange 58 is frequently positioned proximally beyond the reach of barrel rim 30. By contrast, as shown in FIGS. 1, 2, 4, 4A, 5, and others, ring 77 need not extend proximally to the same extent beyond barrel rim 30. This positioning of ring 77 between proximal end 33 and distal end 35 of barrel 20 creates a relatively shorter distance between barrel rim 30 and ring 77, and further promotes stability and control in the use of ergonomic syringe 10. It will also be appreciated that, in some embodiments, the distance between ring 77 and the distal end 52 of plunger 26 will remain constant, particularly when ring 77 is integrally formed with plunger 26.

In some embodiments, slide member 28 includes a first elongate arm 74 and a second elongate arm 75, as shown in FIG. 6. The elongate arms may be positioned 180° apart as defined by an outer rim of ring 77. Alternatively, a single elongate piece (not shown) could be used in place of first and second elongate arms, 74, 75. Alternatively, syringe 10 could be constructed with slide member 28 having three or more elongate pieces positioned relative to each other at angles as selectably desired by a user, for example 120° as defined by the above-mentioned outer rim, or any number of elongate arms in like fashion. In all such embodiments, at one end the elongate arms 74, 75 and/or elongate piece are attached to the proximal facing surface 78 of ring 77, while at the other end they are attached to a distal facing surface 61 of the plunger flange 58, which consistently maintains the correspondence of movement between slide member 28 and plunger 26, such that as ring 77 moves, so does plunger 26. Attachment is accomplished through any of a number of methods known to those having ordinary skill in the art, and is typically performed at the time of fabricating plunger 26, though this is not required.

In some embodiments, elongate arms 74, 75 are straight, and extend parallel to axis 22, as illustrated in FIG. 6. Alternatively, elongate arms 74, 75 extend at an angle to axis 22. In some embodiments, ring 77 is a circular member. Alternatively, ring 77 comprises a flange extending outward relative to axis 22, and otherwise having a cross-section of straight-line segments forming a polygonal shape (not shown), e.g., rectangular, octagonal or hexagonal. The latter configuration limits rolling motion of syringe 10, thereby preventing it from rolling off of a surface when not in use.

Figure 7:
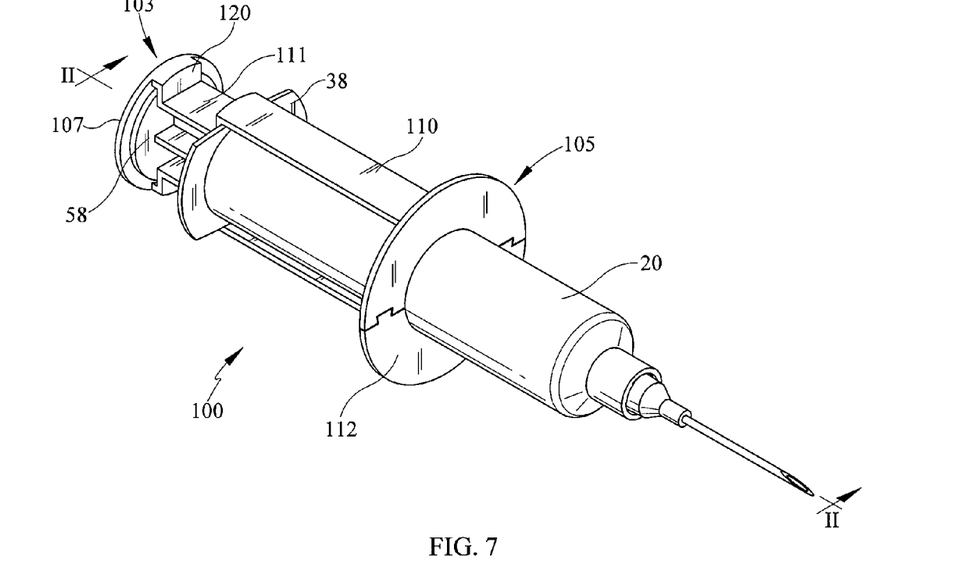
FIG. 7 is a perspective view of an adaptor fitted over a conventional syringe, according to multiple embodiments and alternatives.
Figure 7A:
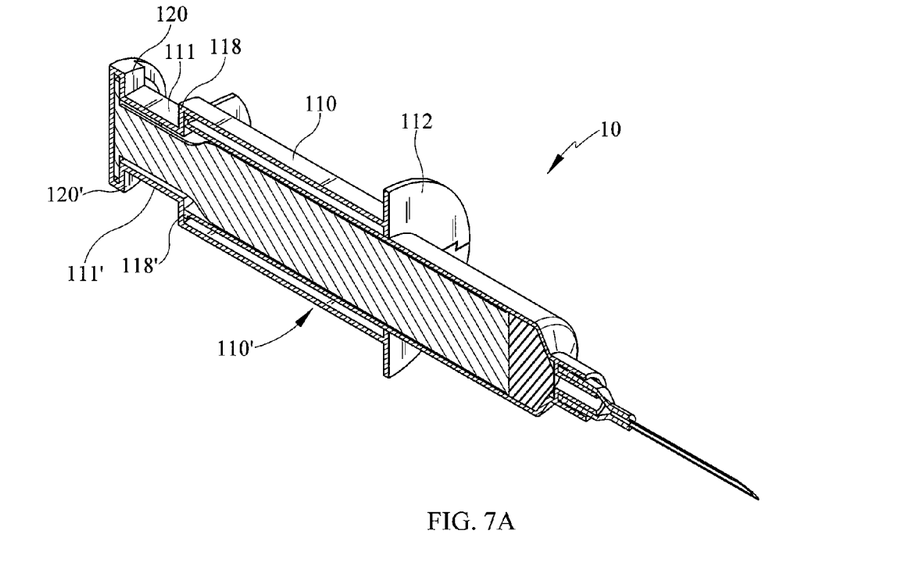
FIG. 7A is a cross-sectional perspective view of an adaptor fitted over a conventional syringe, in which the view is taken along line II-II of FIG. 7, according to multiple embodiments and alternatives.

Whereas the above descriptions and teachings relate to an ergonomic syringe 10, the following relate to an ergonomic adaptor 100 (sometimes referred to herein simply as, adaptor) for use with an existing conventional syringe, and which can be reusable. The conventional syringe may include a barrel 20, plunger 26, webs 27, sealing member 56, and plunger flange 58 as described herein. FIG. 7 provides a view of ergonomic adaptor 100 fitted over a conventional syringe, which includes a barrel 20 with barrel flange 38, and FIG. 7A is a cross-sectional view of the same. Adaptor 100 has a proximal end 103 and a distal end 105. It also includes a first elongate arm 110 and a second elongate arm 111. In some embodiments, adaptor 100 is configured to circumvent barrel flange 38 as it establishes a mechanical connection between a portion of a ring 112 (in the form of a radially extending flange) and plunger flange 58. Techniques available for finger placement on barrel 20 and ring 112 are substantially similar to those described above with respect to ergonomic syringe 10, and ring 77, as is the option between flat and curved surfaces for ring 112, and the geometric shapes for ring 112.

Figure 8:
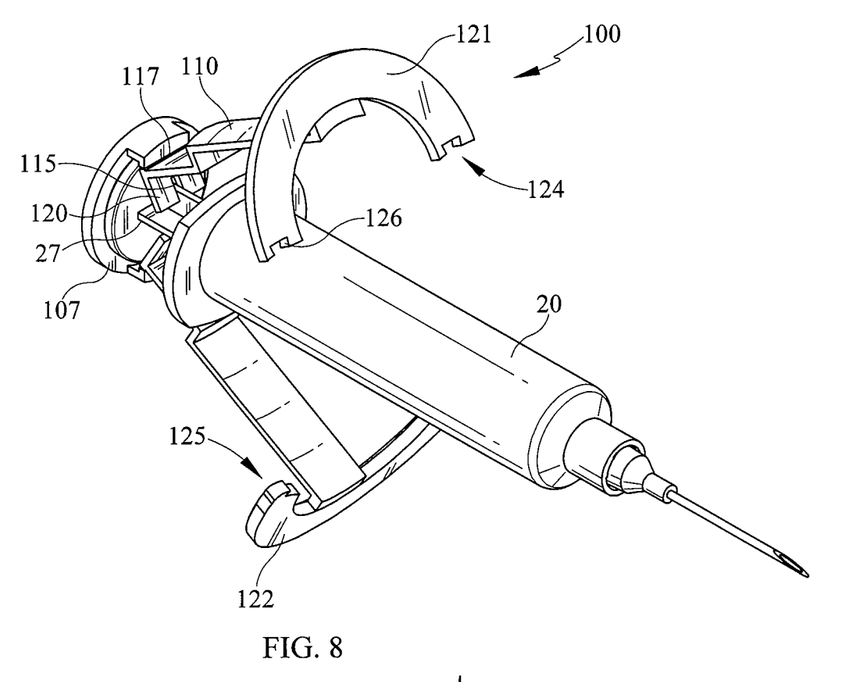
FIG. 8 is a side elevation view of an adaptor partially fitted over a conventional syringe, according to multiple embodiments and alternatives.

As also shown in FIG. 7 and FIG. 7A, in some embodiments, first elongate arm 110 is straight as it extends from ring 112 in a proximal direction. Adaptor 100 further comprises a first extension elbow 118, preferably positioned at an approximately 90° angle to first elongate arm 110, which connects elongate arms 110, 111. Moving proximally along adaptor 100, a second extension elbow 120 is attached to second elongate arm 111, and preferably these two members are likewise positioned at an approximately 90° angle. In some embodiments, as illustrated in FIG. 8 second elongate arm 111 and second extension elbow 120 are joined to second ring 107 through use of a hinge 117 forming a hinged joint, which allows for adjustable movement radially of second extension elbow 120, thus enabling adaptor 100 to be fitted over and/or removed from plunger flange 58 of an existing syringe. Hinge 117 may be formed from the same material used in forming the other pieces of adaptor 107. In some embodiments, hinge 117 is formed as a living hinge from polyethylene, polypropylene, or other suitable thermoplastic having sufficient fatigue resistance. When fitting the adaptor over the syringe, the radial movement of extension elbow 120 is inward toward the barrel, while radial movement away from the barrel is for removing it. With adaptor 100 securely fitted over plunger flange 58, the exertion of force on ring 112 produces axial movement of adaptor 100, thereby causing plunger flange 58, plunger 26 and sealing member 56 to move a substantially equal distance along the same axis.

Adaptor 100 thus is suitable to achieve and maintain a functional and relatively snug fit with many forms of a conventional syringe. In some embodiments, a first elongate arm 110' and second elongate arm 111' are essentially configured in the same way as with arms 110, 111, including a first extension elbow 118' and second extension elbow 120'. In some embodiments, first elongate arms 110, 110' are positioned 180° apart as defined by the outer periphery of ring 112. Proximal ends of extension elbows 120, 120' are joined together by the second ring 107, which fits over proximal facing surface 63 of plunger flange 58, such that second elongate arms 111, 111' are also positioned 180° apart. As stated in connection with the syringe, the present embodiments are not limited to a certain number of extension arms.

FIG. 8 provides a side elevation view of adaptor 100 partially fitted over a conventional syringe. In some embodiments, ring 112 of adaptor 100 consists of two semi-circular members, 121, 122. Given that there are two members, some embodiments include more than one first elongate arm 110 (another being denoted as 110'), more than one second elongate arm 111 (another being denoted as 111'), more than one first extension elbow (118'), more than one second extension elbow (120'), and more than one hinge (117'). First semi-circular member 121 is attached to first elongate arm 110, and second semi-circular member 122 is attached to first elongate arm 110'. However, in some embodiments (not shown), ring 112 is a unitary member with an opening sized to fit snugly around the distal end 35 of barrel 20 (in the same way as described with FIG. 1). Whether one-piece or multiple pieces, preferably ring 112 encircles barrel 20.

Turning back to FIG. 7 and FIG. 7A, the position of adaptor 100 is then adjusted axially along the length of barrel 20, until second extension elbows 120, 120' are positioned for contact and operational engagement with plunger flange 58. Second elongate arms 111, 111' are then moved radially toward each other and towards barrel 20, and in this way placed into mechanical contact with or otherwise attached to plunger flange 58. In this placement, the correspondence of movement is consistently maintained between adaptor 100 and plunger 26, such that as ring 112 moves, so does the plunger 26.

Whereas FIG. 7 shows barrel 20 completely encircled by ring 112, in FIG. 8 semi-circular members 121, 122 are disengaged from each other. Once engaged, or otherwise connected, the two members form a ring that encircles barrel 20. As FIG. 8 shows, first member 121 contains spaces 124, 126 that are capable of mating with first latch 123 (hidden behind barrel 20 in the drawing figure) and second latch 125, respectively, of second member 122. Spaces 124, 126 and latches 123, 125, respectively, are of suitable size and shape to allow them to snap fit into place securely in order to complete the encirclement of barrel 20 by ring 112. Further, in some embodiments, a slot, 115, or plurality of slots, are formed along a surface of second extension elbows 120, 120', with each slot 115, being substantially perpendicular to second elongate arms 111, 111', for accommodating the webs 27 of plunger 26.

Once adaptor 100 is fitted onto an existing syringe, the use is substantially the same as described above for ergonomic syringe 10. Preferably, adaptor 100 is designed for use with conventional syringes of varying designs and/or capacities, although it may also be designed specifically for and matably used with an individually designed syringe. In some embodiments, adaptor 100 is reusable, in that it can be removed from one syringe and attached for use with a different syringe, which is generally of similar size and capacity. Although not shown, various alternatives exist for joining semi-circular members 121, 122, such that they can be easily detached for removal of adaptor 100. For example, members 121, 122 may be joined by latch with latch post and latch tab, clasp, dovetail joint, compression snap, interference snap, or cantilevered clip with angled hook face (not shown), all of which are known in the art. The joining structures can be incorporated into members 121, 122 at fabrication.

One way of removing adaptor 100 from a syringe is by grasping each semi-circular member 121, 122, and exerting an opposing force on each sufficient to pull them apart. Alternatively, adaptor 100 can be designed so that a surface of semi-circular member 121 overlays a surface of second semi-circular member 122, and joined with a screw that fits into a threaded hole formed in both surfaces, and further secured by the use of, e.g., a nut.

Figure 8A:
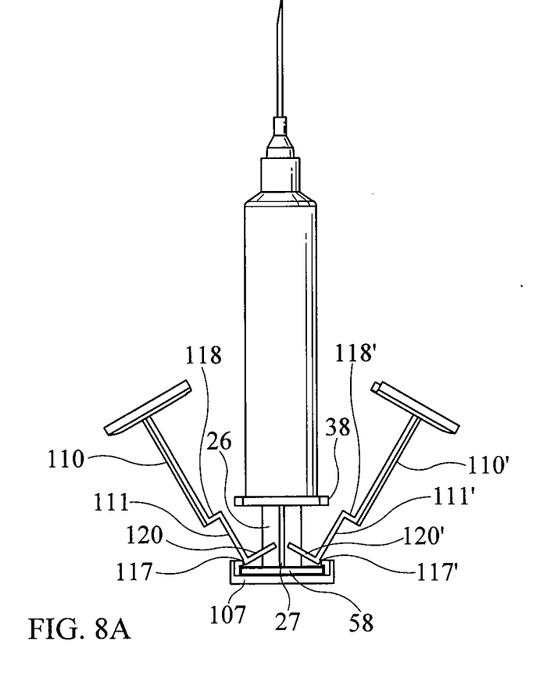
FIG. 8A is a perspective view of an adaptor partially fitted over a conventional syringe, according to multiple embodiments and alternatives.

FIG. 8A provides a different view of adaptor 100 partially fitted over a conventional syringe. As previously mentioned, in some embodiments, second extension elbows 120, 120' are attached to second ring 107 at hinge 117, thus enabling radial movement. Adaptor 100 is fitted over the syringe through radial movement inward toward the barrel, while radial movement away from the barrel is for removing it. Attachment of the extension elbows 120, 120' to second ring 107 is accomplished through any of a number of methods known to those having ordinary skill in the art, and is typically performed at the time of fabricating adaptor 100, though this is not required.

Figure 9:
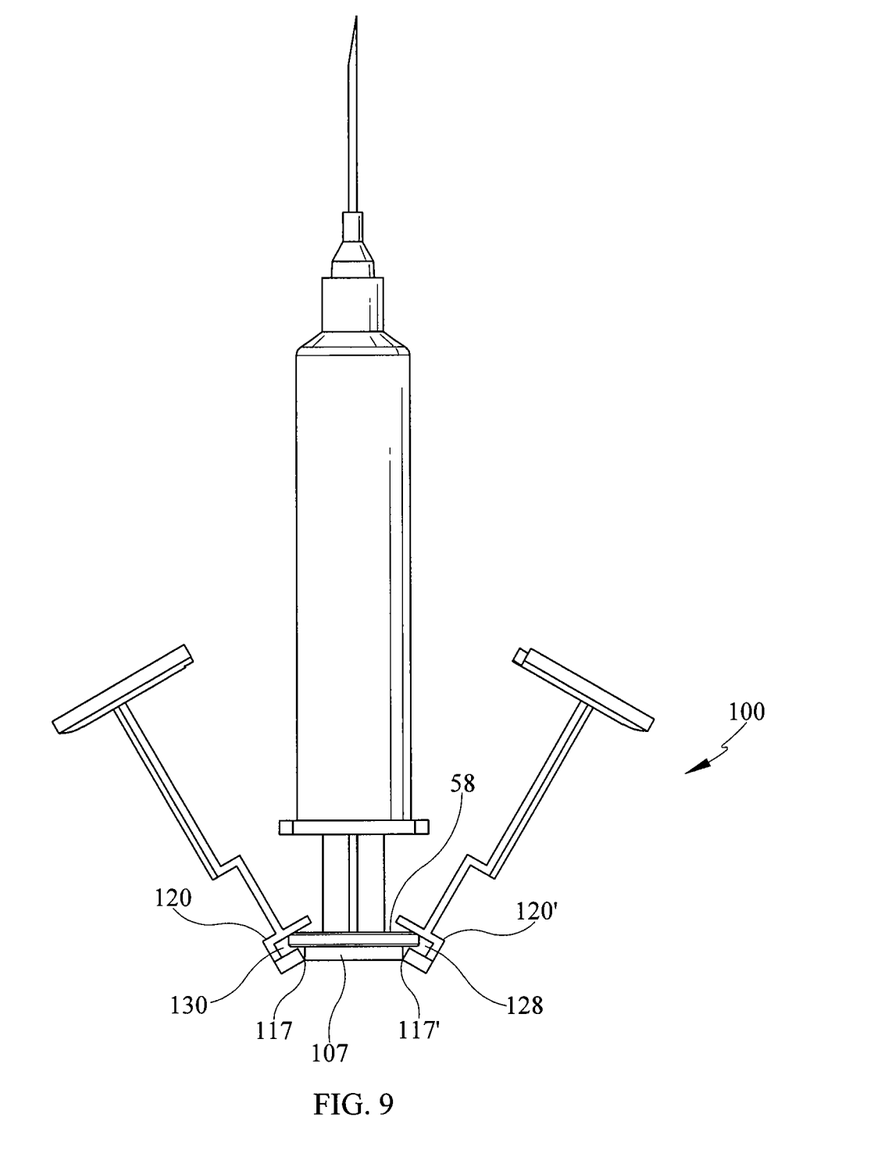
FIG. 9 is a plan view of an adaptor partially fitted over a conventional syringe, according to multiple embodiments and alternatives.

FIG. 9 provides a plan view of adaptor 100 partially fitted over a conventional syringe in an alternative embodiment. In this configuration, radial movement relative to axis 22 of each of second extension elbows 120, 120' is for fitting adaptor 100 over an existing syringe, or for removal depending on the direction of movement. Extension elbows 120, 120' are attached to second ring 107 at hinges 117, 117', and the hinges are configured to allow radial movement as described in connection with other embodiments for adaptor 100. In the embodiment of FIG. 9, however, the location of hinge 117 is inferior to plunger flange 58, whereas in FIG. 8A the location is superior. Accordingly, in FIG. 9, each of extension elbow 120, 120' further comprises a first notch 128 and second notch 130, respectively, which are appropriately sized and adapted to releasably secure extension elbows 120, 120' to the sides of plunger flange 58.

With reference to prior figures, including FIG. 2A, FIG. 5, and FIG. 7, respectively, further description is now provided about the operation of an ergonomic syringe 10. The description of the apparatus in operation would be substantially the same for a conventional syringe with adaptor 100. To withdraw fluid, a user typically grips ergonomic syringe 10 with two or more fingers near distal end 35 (or, in certain embodiments, at contoured barrel 21) of barrel 20 and then inserts needle 24 into a source from which fluid is to be withdrawn, which can be a patient. Then the user places a third finger in contact with distal facing surface 79 of ring 77 (according to FIG. 2A, or ring 112 in FIG. 7), and exerts sufficient proximal force thereto in order to partially withdraw plunger 26 from barrel 20, thus withdrawing fluid from the patient or other source through the movement of plunger 26 in a proximal direction relative to barrel 20, along axis 22.

Once a desired quantity of fluid is withdrawn, the extension of the finger in contact with ring 77 (or, 112 in the adaptor embodiments), away from the fingers in contact with barrel 20, ceases. At that point, if the user desires, the position of the ring is maintained and she then removes needle 24 from the patient. Throughout this sequence, a user has one hand free and is available to provide auxiliary support to the operation as needed (e.g. support of patient's limb). Still, a user does not have to reposition the fingers of the hand in contact with barrel 20 in order to contact distal facing surface 79 and withdraw plunger 26. This facilitates a stable and consistent one-handed technique for withdrawing fluid from a patient.

As referenced in FIG. 2, needle 24 has opening 23 at its proximal end, in the form of beveled edge 25. When inserting the needle into the patient, i.e., passing it through the skin and into the blood vessel, it is desirable to have beveled edge 25 facing upward. The fact that ring 77 (112) completely encircles the outer cylindrical area of barrel 20 facilitates a user in keeping the beveled edge in the upward position. But with a conventional syringe, not having ring 77 (112) it is possible for plunger flange 58 to be oriented where a user cannot easily make suitable contact with its surface 112 (e.g., where a plunger web 27 reduces available contact area for finger positioning on plunger flange 58). In order to adjust to that situation, with a conventional syringe a user would have to rotate barrel 20 in order to position plunger flange 58 in a location more accessible to her finger(s). However in the present embodiments, in rotating barrel 20, beveled edge 25 of opening 23 may no longer be facing upward in the desired orientation for insertion into the patient. In such situation, beveled edge 25 and, therefore, needle opening 23, are not suitably oriented for entering the skin. However, with ring 77 (112) completely encircling barrel 20, this type of problem is not encountered because a user is free to position the third finger at any location radially along ring 77 (112) as is more comfortable, feasible, or accessible, in order to apply force needed to withdraw plunger 26.

It will also be understood that in may embodiments, for both the ergonomic syringe and the adaptor as described and claimed herein, ring 77 (112) provides additional surface area for contact by the user compared to the area of distal facing surface 61 of plunger flange 58 (see FIG. 5) as would be found on a conventional syringe. The additional surface area on ring 77 (112) promotes improved finger-to-ring contact. This reduces the chances of the finger slipping compared to when a user must contact plunger flange 58 in order to move plunger 26 along axis 22. Moreover, this additional contact surface area on ring 77 (112) reduces the pressure on the finger as it applies force to move the plunger proximally. In some embodiments, a traction-enhancing material is adhered upon either or both surfaces of ring 112, which further promotes finger-to-ring contact in order to avoid slippage. Ring 112 can be positioned to reduce overall range of motion that a finger in contact with a surface of ring 112 must travel relative to the other fingers in order to apply sufficient force to withdraw plunger 26 and, in so doing, to withdraw fluid from a patient. Additionally, this more ergonomic positioning of the hand/fingers allows greater force to be exerted for moving ring 112, which can provide advantages for users having limited hand/finger strength.

In some instances, plunger 26 may only have to move 1-2 centimeters in order to withdraw the desired amount of fluid. However, in other instances, plunger 26 must travel significantly longer distances. Longer distances equates to the need for greater extension of the finger in order to move the plunger. In this respect, whatever distance plunger 26 must travel, with the present embodiments, a user's fingers extend through a smaller range of motion while pushing the ring to move the plunger than when they do when using a conventional syringe. This increases the amount of stability, control and comfort for the user, as well as for the patient. Moreover, this improved operation reduces the stress on the user's hand/fingers, thus reducing the likelihood of injury associated with repetitive usage.

The foregoing descriptions of multiple embodiments and alternatives are meant to illustrate, rather than to limit the scope of what has been disclosed herein. While multiple and varying embodiments of the presently disclosed technology have been illustrated and described herein, it will be apparent to those having ordinary skill in the art that modifications can be made. To the extent not otherwise disclosed herein, materials for the syringe and adaptor may be the same as those used for conventional design. Moreover, while individual features of various embodiments may be shown in some drawings but not in others, skilled in the art will recognize that individual features of one embodiment are capable of being combined with any or all features of another embodiment.

Thus, it is to be understood that these embodiments are not limited in their application to the details of the teachings and descriptions set forth herein, or as illustrated in the drawings. Rather, it will be understood that an ergonomic syringe, and adaptor, are capable of other embodiments and of being practiced or of being carried out in various ways. It will also be understood that certain terminology used herein is for the purpose of description and should not be regarded as limiting. The use herein of "including," "comprising," "e.g.," "containing," or "having" and variations of those words is meant to encompass the items listed thereafter, and equivalents of those, as well as additional items.

I claim:

1. An adaptor for a syringe having an at least partially hollow barrel and a plunger, the barrel having a proximal end and a distal end, with an aperture positioned at the proximal end for accepting the plunger, and the plunger being adapted for insertion into the aperture for movement axially within the barrel, comprising:
   at least one ring; and
   a plurality of elongate arms positioned axially along the exterior of the barrel, each having a first end attached to the ring and a second end attached to the plunger;
   wherein exerting force axially upon the at least one ring produces axial movement of the adaptor along the barrel, thereby causing the plunger to move a substantially equal distance as the ring along the same axis;
   and wherein at least one of the elongate arms further comprises a slot spatially adapted to accommodate a web of the plunger.

2. An adaptor for a syringe having an at least partially hollow barrel and a plunger, the barrel having a proximal end and a distal end with an aperture positioned at the proximal end for accepting the plunger and a barrel flange positioned near the proximal end of the barrel; and the plunger being adapted for insertion into the aperture for movement axially within the barrel, comprising:

a first ring and a second ring, one being positioned closer to the distal end of the barrel than the other, wherein at least one of the rings comprises a plurality of members arranged to form a detachable connection; and a plurality of elongate arms extending axially along the exterior of the barrel;

at least one extension elbow positioned between the first ring and the second ring for connecting two elongate arms;

wherein exerting force axially upon the ring positioned closer to the distal end of the barrel produces axial movement of the adaptor along the barrel, thereby causing the plunger to move a substantially equal distance along the same axis.

3. The adaptor of claim 2, wherein the detachable connection is formed by means chosen from the group latch, clasp, dovetail joint, compression snap, and interference snap.

4. The adaptor of claim 2, wherein a hinge joins the at least one elongate arm and the at least one extension elbow to the second ring.

5. The adaptor of claim 2, wherein the at least one extension elbow further comprises a slot spatially adapted to accommodate a web of the plunger.

6. The adaptor of claim 1, further comprising a second ring attached to the plunger, wherein the elongate arms connect the first ring to the second ring.

7. The adaptor of claim 1, wherein the at least one ring comprises a plurality of members, each arranged for detachable connection with the other.

8. The adaptor of claim 7, wherein the detachable connection is formed by means chosen from the group latch, clasp, dovetail joint, compression snap, and interference snap.

* * * * *

UNITED STATES PATENT AND TRADEMARK OFFICE
CERTIFICATE OF CORRECTION

| | | |
|---|---|---|
| PATENT NO. | : 9,067,023 B2 | Page 1 of 1 |
| APPLICATION NO. | : 13/676810 | |
| DATED | : June 30, 2015 | |
| INVENTOR(S) | : Gina E. Bertocci | |

It is certified that error appears in the above-identified patent and that said Letters Patent is hereby corrected as shown below:

On the Title Page of the Letters Patent, Applicant Item (71), University of Louisville Research Foundation, Inc., delete "Nashville, TN" and add "Louisville, KY".

Signed and Sealed this
Third Day of November, 2015

Michelle K. Lee
*Director of the United States Patent and Trademark Office*